(12) United States Patent
Bocquet et al.

(10) Patent No.: US 11,541,359 B2
(45) Date of Patent: Jan. 3, 2023

(54) USE OF NANOPOROUS CARBON MEMBRANES FOR SEPARATING AQUEOUS/ORGANIC MIXTURES

(71) Applicants: PARIS SCIENCES ET LETTRES—QUARTIER LATIN, Paris (FR); UNIVERSITE PARIS DIDEROT PARIS 7, Paris (FR); CENTRE NATIONAL DE LA RECHERCHE SCIENTIFIQUE (CNRS), Paris (FR); SORBONNE UNIVERSITE, Paris (FR)

(72) Inventors: Lyderic Bocquet, Paris (FR); Alessandro Siria, Paris (FR); Benoit Laborie, Paris (FR); Hiroaki Yoshida, Paris (FR); Simon Gravelle, Londres (GB)

(73) Assignees: Paris Sciences et Lettres, Paris (FR); Université Paris Cité, Paris (FR); Centre National De La Recherche Scientifique (CNRS), Paris (FR); Sorbonne Universite, Paris (FR)

( * ) Notice: Subject to any disclaimer, the term of this patent is extended or adjusted under 35 U.S.C. 154(b) by 87 days.

(21) Appl. No.: 16/497,977
(22) PCT Filed: Mar. 27, 2017
(86) PCT No.: PCT/EP2017/057183
§ 371 (c)(1),
(2) Date: Sep. 26, 2019
(87) PCT Pub. No.: WO2018/177498
PCT Pub. Date: Oct. 4, 2018

(65) Prior Publication Data
US 2021/0008504 A1 Jan. 14, 2021

(51) Int. Cl.
*B01D 71/02* (2006.01)
*B01D 61/02* (2006.01)
(Continued)

(52) U.S. Cl.
CPC ......... *B01D 71/021* (2013.01); *B01D 61/027* (2013.01); *B01D 61/362* (2013.01);
(Continued)

(58) Field of Classification Search
None
See application file for complete search history.

(56) References Cited

U.S. PATENT DOCUMENTS

2013/0270188 A1* 10/2013 Karnik ................ G01N 15/082
210/650

FOREIGN PATENT DOCUMENTS

| GB | 723233 A | * 2/1955 | ............ B01D 71/38 |
|---|---|---|---|
| WO | WO 2014/027197 | 2/2014 | |
| WO | WO 2015/075451 | 5/2015 | |

OTHER PUBLICATIONS

Yanan Hou, Zhijun Xu, and Xiaoning Yang, Interface-Induced Affinity Sieving in Nanoporous Graphenes for Liquid-Phase Mixtures, The Journal of Physical Chemistry C 2016 120 (7), 4053-4060 (Year: 2016).*

(Continued)

*Primary Examiner* — Jason M Greene
*Assistant Examiner* — Eric J McCullough
(74) *Attorney, Agent, or Firm* — Barnes & Thornburg LLP; G. Peter Nichols

(57) ABSTRACT

The invention relates to the extraction of organic compounds from mixtures of said compounds with water, using a nanoporous carbon membrane. The invention can be used in any field where it is desired to separate an organic compound of interest from water, such as the drying of alcohols or alkanes.

8 Claims, 1 Drawing Sheet

Figure 1:
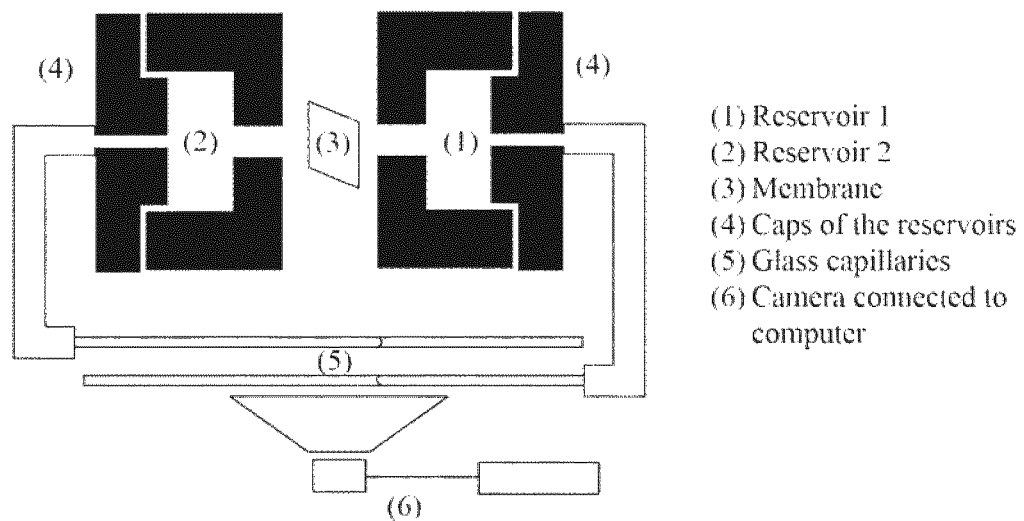

(1) Reservoir 1
(2) Reservoir 2
(3) Membrane
(4) Caps of the reservoirs
(5) Glass capillaries
(6) Camera connected to computer

(51) Int. Cl.
  *B01D 61/36* (2006.01)
  *B01D 69/10* (2006.01)
  *C07B 63/00* (2006.01)
(52) U.S. Cl.
  CPC .............. *B01D 69/10* (2013.01); *C07B 63/00* (2013.01); *B01D 2325/02* (2013.01)

(56) References Cited

OTHER PUBLICATIONS

Wei-Song Hung, et al., Pressure-assisted self-assembly technique for fabricating composite membranes consisting of highly ordered selective laminate layers of amphiphilic graphene oxide, Carbon, vol. 68, 2014, pp. 670-677 (Year: 2014).*

Huang, L., et al. (2016), Reduced Graphene Oxide Membranes for Ultrafast Organic Solvent Nanofiltration. Adv. Mater., 28: 8669-8674. (Year: 2016).*

Gravelle et al., "Carbon membranes for efficient water-ethanol separation," Cornell University Library, 201 Olin Library Cornell University Ithaca, NY 14853, pp. 1-8 (Sep. 7, 2016).

Liu et al., "Graphene oxide membrane for liquid phase organic molecular separation," Carbon, 77: 933-938 (Oct. 1, 2014).

Search Report & Written Opinion issued in Int'l App. No. PCT/EP2017/057183 (2017).

* cited by examiner

USE OF NANOPOROUS CARBON MEMBRANES FOR SEPARATING AQUEOUS/ORGANIC MIXTURES

CROSS REFERENCE TO RELATED APPLICATIONS

This application is a U.S. nationalization under 35 U.S.C. § 371 of International Application No. PCT/EP2017/057183, filed Mar. 27, 2017 the entire contents of which is incorporated herein by reference.

The present invention relates to uses of carbon-based membranes for the separation of aqueous/organic mixtures, such as water/alcohol or water/alkane mixtures.

The removal of water (also referred to herein as "dehydration") from water/organic liquid mixtures is required in a variety of industrial processes.

One example is alcohol dehydration in the production of alcohols, such as ethanol and butanol, from biomass. A first step in the process of production of these bioalcohols involves microbial fermentation of sugars derived from biomass. This fermentation produces an aqueous solution with an alcohol concentration of usually about 5-15% wt.

Higher alcohol concentrations can be obtained by means of conventional distillation. However, the efficiency of this method is limited due to the formation of a water-alcohol azeotrope. For instance, ethanol forms with water an azeotrope containing 95.5% ethanol and 4.5% water (by weight), which precludes obtaining a distillate with an ethanol content higher than 95.5%.

To achieve the higher level of purity which is required for most uses, such as vehicle fuel or fuel additive, a further dehydration step is necessary.

Various solutions exist for the dehydration of alcohol (for review see Huang et al., 2008). The most commonly used methods include for instance, azeotropic distillation and membrane separation.

Azeotropic distillation involves adding a third component, called "entrainer", which forms a ternary azeotrope with the two components to be separated. This induces a change in their relative volatilities, allowing separation to occur in the distillation system. In the case of ethanol-water azeotropes, the most commonly used entrainers are benzene, toluene, and cyclohexane.

The drawbacks of azeotropic distillation are its high energy cost, and the need of a large and complex equipment, as well as the safety concerns generated by the toxicity or flammability of the products used as entrainers.

Pervaporation is a method for the separation of mixtures of liquids by partial vaporization through a dense non-porous membrane. The separation mechanism is a solution-diffusion through the membrane. The feed liquid mixture is in direct contact with one side of the membrane and the permeate is removed in a vapor state from the opposite side. The membrane can be either hydrophilic (water perm-selective) or hydrophobic (alcohol perm-selective), but in general, most membranes used for alcohol dehydration are hydrophilic due to the smaller molecular size of water.

Currently, pervaporation is considered as one of the most effective and energy-saving processes for the separation of ethanol and water.

However, this method still requires to heat the system up to ~80° C. for water-ethanol separation. Thus, although lower than in the case of conventional or azeotropic distillation, the energy cost is not negligible.

Another membrane-based separation method is reverse osmosis. This method uses a semi-permeable membrane which allows passage of one component of a solution while preventing passage of the other. In spontaneous osmosis, the component which can freely cross the membrane (usually the solvent) flows from the side where its concentration is higher to the side where its concentration is lower. In reverse osmosis, pressure is applied in the opposite direction to the spontaneous osmosis process, resulting in a reversion of the direction of this flow. As a result, the solvent can diffuse through the membrane and is found in the permeate, while the solute concentrates in the feed side of the membrane.

Reverse osmosis is currently the most important desalination technology due in particular to its very low energy requirement in comparison with thermal desalination. In the case of alcohol dehydration, the same advantages would be expected, since no phase change is needed for the separation of alcohol from water. However, the use of reverse osmosis, and especially the choice of appropriate semi-permeable membranes is more problematic when the species to separate are neutral and have very similar size, such as ethanol and water.

Yet, there have been a few attempts to use reverse osmosis to separate water-ethanol mixtures. Because of the larger size of the ethanol molecules, most of the membranes are selectively permeable to water (Hu et al., 2013), with one report of the use of a membrane selectively permeable to ethanol. (Tanimura et al. 1990).

Another problem is the high osmotic pressure of concentrated ethanol solutions. Choudhury et al (1985) describe a method using a membrane impermeable to ethanol and permeable to water; the feed input to the membrane is a water/ethanol mixture. The separated water is eliminated in the permeate, and the concentration of ethanol in the mixture increases as the reverse-osmosis process advances. However, when the ethanol concentration in the mixture is high, very huge osmotic pressure occurs, which is difficult to overcome by means of reasonable working pressure. Particularly, it is almost impossible to increase the ethanol concentration above the azeotropic point of 95.5% (high pressure of about 3000 bars is necessary).

Recently, a new type of semi-permeable membranes has attracted a lot of interest: nanoporous carbon membranes.

Nanoporous carbon membranes include carbon nanotube membranes, nanoporous graphene membranes, and multilayer graphene oxide membranes. All these materials can show similar properties of selective permeability and it has been proposed to use them as molecular sieves in applications involving membrane separation, such as nanofiltration, desalination, pervaporation, etc.

Carbon nanotube membranes consist of two pierced graphene sheets connected by short carbon nanotubes of defined diameter. Their practical application is however limited due to the complexity of their manufacture.

Nanoporous graphene membranes consist of a single sheet of graphene with nanopores of defined size. However, it is still difficult to obtain large graphene sheets with a pre-defined pore size and a high pore density.

Graphene oxide (GO) membranes are composed of stacked GO nanosheets separated by interconnected nanochannels which form the pores allowing selective permeation through the membrane. They can be produced relatively easily and cheaply by depositing GO solutions onto various supports by spraying, dip coating, spin coating, vacuum filtration, etc., and are currently the most commonly used. Further, GO sheets can converted to graphene-like reduced GO (rGO) sheets, with electrical, thermal, mechanical, and surface properties similar to those of pristine graphene.

It has been proposed to use graphene-based membranes, in particular GO and rGO membranes as separation membranes in a broad variety of applications (Liu, Jin et al. 2015), including dehydration methods such as vapor phase separation or pervaporation (PCT WO 2014/027197), or water purification (PCT WO 2015/075451).

Graphene-based membranes have been reported to be selectively permeable to water. Nair et al., 2012 report that GO membranes can allow unimpeded permeation of water while being can be completely impermeable to other liquids, vapors, and gases, including helium. Liu, Arabale et al. (2014) studied the permeation through GO membranes of mixtures of organic solvents and water. They report that the permeation rates of alcohols such as ethanol, 1-propanol and 2-propanol (IPA) were about 80 times lower than that of water.

The inventors have found that while nanoporous carbon membranes are in general permeable to both water and ethanol when they are used as pure components, they may become fully impermeable to water while keeping a high permeability to ethanol, in the presence of water-ethanol mixtures. This is unexpected, given the largest size of the ethanol molecule when compared to water. This allows achieving water-ethanol separation by removing ethanol from an ethanol-water mixture, in contrast to the prior art dehydration methods which rely upon the removal of water.

Without wishing to be bound by theory, it is believed that the basic mechanism for this specific separation lies in a preferred adsorption of ethanol as compared to water on the carbon surface. The adsorbed ethanol fills the pores of membrane, preventing penetration of water. As a result, only ethanol can flow through the membrane.

An object of the present invention is the use of a nanoporous carbon membrane for separating water from an organic compound in a fluid mixture, by extraction of said organic compound from said mixture.

The present invention also provides a method for extracting an organic compound from a fluid mixture of said organic compound with water, wherein said method comprises:

contacting said mixture with one side of a nanoporous carbon membrane;
recovering the organic compound from the other side of said nanoporous carbon membrane.

For carrying out the method of the invention one can use any separation device comprising two compartments separated by the nanoporous carbon membrane. The mixture to be separated is placed in a first compartment, and the extracted organic compound is recovered in the second.

The fluid mixture can be a liquid mixture or a gaseous mixture.

According to a preferred embodiment, the nanoporous carbon membrane is activated before its use, by contacting it with a pure preparation of the compound to be extracted, during at least 5 minutes, preferably during 5 to 30 minutes.

Said organic compound can be any water-soluble or water-miscible compound having higher affinity than water for the surface of the membrane pores.

It can be in particular an alcohol or an alkane. For instance, it can be a $C_1$-$C_{12}$, more preferably a $C_1$-$C_8$, still more preferably a $C_1$-$C_6$, and even more preferably a $C_1$-$C_4$, alcohol, or a $C_1$-$C_{12}$, more preferably a $C_1$-$C_8$, still more preferably a $C_1$-$C_6$, and even more preferably a $C_1$-$C_4$, alkane. In both cases, it can have a linear or branched carbon chain. In the case of an alcohol, it can be a monoalcohol, or a polyol, in particular a glycol; it can also be a primary, secondary, or tertiary alcohol.

Examples of preferred alcohols are methanol, ethanol, propanol, butanol, ethylene glycol, propylene glycol, glycerol.

Examples of preferred alkanes are methane, ethane, propane, butane.

The nanoporous carbon membrane can be a carbon nanotube membrane, a nanoporous graphene membrane, or a multilayer GO or rGO membrane.

The pore size should be above 0.7 nm and below 1.5 nm, preferably below 1.4 nm, more preferably below 1.3 nm, still more preferably below 1.1 nm, and even more preferably below 1.1 nm.

The "pore size" herein refers to the pore diameter in the case of carbon nanotubes and nanoporous graphene membranes, and to the width of the inter-layer gaps in the case of multilayer GO or rGO membranes.

Typically, the nanoporous carbon membrane has a thickness of from 0.05 μm to 1 μm, preferably of from 100 to 500 nm, in the case of a carbon nanotube membrane.

In the case of a multilayer GO or rGO membrane, it comprises at least 2, preferably at least 3, and up to 300 layers of GO or rGO sheets, and has a thickness of from 0.05 to 1 μm, preferably of about 0.1 μm.

The nanoporous carbon membrane can be used alone, or placed on a porous support layer. Said porous support layer should allow the permeation of the organic compound to be separated from water.

The porous support layer can be made of a non-reactive polymeric material, for instance a fluoropolymer such as polyvinylidene fluoride (PVDF) or polytetrafluoroethylene (PTFE), or a porous polycarbonate, or mixed cellulose ester or cellulose acetate. It can also be made of a porous ceramic material such as an alumina, silica, or titanium dioxide based porous ceramic, by way of non-limitative examples.

Preferably said porous support layer has a pore size of from 0.05 to 1 μm, more preferably of from 0.1 to 0.5 μm and a thickness of from 30 to 300 μm, more preferably of from 100 to 200 μm.

When the nanoporous carbon membrane is placed on a porous support layer, the resulting combined filtration membrane can be used in any orientation, i.e. either the carbon membrane face, or the porous support face can be contacted with the mixture to be separated. Combined filtration membranes where the carbon membrane is placed on both sides of the porous support layer, or alternatively placed between two porous support layers can also be used, as well as multilayered combined filtration membranes alternating two or more layers of carbon membrane with two or more layers of porous support.

The present invention can be used in methods such as pervaporation, liquid-liquid extraction or reverse osmosis, and in any field where it is desired to separate an organic compound of interest from water. For instance, it can be used in the industry of biofuel for the drying of alcohols such as ethanol. It can also be used to regenerate the glycol used for dehydration of natural gas and natural gas liquids.

LEGENDS OF THE DRAWINGS

FIG. 1: Sketch of the experimental set up used to measure the osmotic flow through the GO and rGO membranes.

Figure 2:
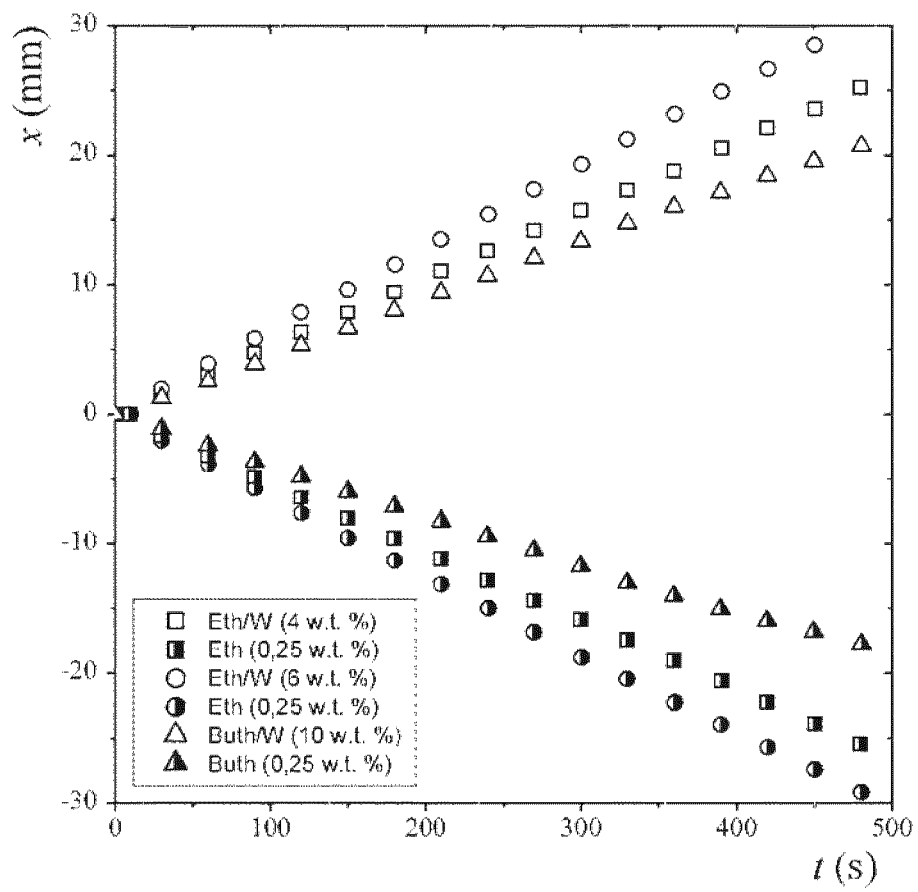

FIG. 2: Plot of the distance from the initial position of the menisci as a function of time for ethanol/water solutions (Eth/W) with two different concentrations of water, and for a butanol/water solution (Buth/W), using a GO membrane (the same result is observed with rGO membranes). Empty symbols correspond to the meniscus connected to reservoir (1) (Eth/W or Buth/W solution). Half filled symbols correspond to the meniscus connected to reservoir (2) (Eth or Buth). The distance in counted negatively when the meniscus moves toward the reservoir.

EXAMPLE

A graphene oxide (GO) and a reduced graphene oxide membrane (rGO) were tested for their permeability to water and ethanol in presence of a water/ethanol mixture, and to water and butanol in presence of a water/butanol mixture.

The GO or rGO membranes are made by deposit of a thin layer (thickness 0.1 μm) of GO on a porous support layer (PVDF with a thickness of 150 μm and a pore size of 0.2 μm), as described by Akbari et al. (2016) or Wang et al. (2012). To obtain rGO membranes, GO membranes are directly reduced using ascorbic acid according to the protocol detailed by Su et al. (2014), or Zhang et al. (2010). The membrane is reduced in a solution of ascorbic acid with concentration of 30 g/L, at 50+/−5° C. for 24 h. Finally, it is dried under vacuum for 1 h. Prior to each experiment, the membrane is dipped into ethanol for a few minutes. Each piece of membrane is approximately 5×5 mm.

The semi-permeable behavior and the resulting separation ability of these membranes are evaluated by measuring the osmotic flow through the membranes, as described below.

The experimental set-up used to measure the flow through a membrane is shown in FIG. 1. The membrane (3) is held between two reservoirs of 1.2 ml. Reservoir (1) is filled with a water/ethanol mixture or a water/butanol mixture. Reservoir (2) is filled with ethanol or butanol (concentration of water 0.25 w.t. %). Each reservoir is connected to a glass capillary (5). In each capillary, the meniscus can move freely according to the fluid flow through the membrane. A camera records the motion of the menisci inside the capillaries (6). The side of the membrane with the GO or rGO coating faces reservoir 1.

The displacement of both menisci from the same initial position is plotted as a function of time. The results for ethanol/water mixtures with two different concentrations of water (4 and 6 w.t. %), and for a butanol/water mixture with a concentration of water of 10 w.t. % are shown on FIG. 2.

It is observed that, for a given concentration the menisci move with the same velocity but in opposite directions. The meniscus connected to the reservoir (2) (Eth) moves towards its reservoir while the one connected to the reservoir (1) (Eth/W) moves away from its reservoir. This shows that there is a flow through the membrane from the higher ethanol concentration side to the lower ethanol concentration side, while there is no reverse flow from the higher water concentration side to the lower water concentration side. This shows that the membrane is semi-permeable to ethanol which is the only species able to flow through it.

REFERENCES

Akbari, A., P. Sheath, S. T. Martin, D. B. Shinde, M. Shaibani, P. C. Banerjee, R. Tkacz, D. Bhattacharyya and M. Majumder; Nature communications 7: 10891 (2016).

Choudhury, J. P., P. Ghosh and B. K. Guha; Biotechnology and Bioengineering 27(7): 1081-1084 (1985).

Hu, M. and B. Mi; Environmental Science & Technology 47(8): 3715-3723 (2013).

Huang, H.-J., S. Ramaswamy, U. W. Tschimer and B. V. Ramarao; Separation and Purification Technology 62(1): 1-21 (2008).

Liu, G., W. Jin and N. Xu; Chem Soc Rev 44(15): 5016-5030 (2015).

Liu, R., G. Arabale, J. Kim, K. Sun, Y. Lee, C. Ryu and C. Lee; Carbon 77: 933-938 (2014).

Su, Y., V. G. Kravets, S. L. Wong, J. Waters, A. K. Geim and R. R. Nair; Nature communications 5: 4843 (2014).

Tanimura, S., S.-i. Nakao and S. Kimura; AIChE Journal 36(7): 1118-1120 (1990).

Wang, J., M. Liang, Y. Fang, T. Qiu, J. Zhang and L. Zhi; Advanced Materials 24(21): 2874-2878 (2012).

Zhang, J., H. Yang, G. Shen, P. Cheng, J. Zhang and S. Guo; Chemical Communications 46(7): 1112-1114 (2010).

The invention claimed is:

1. A method for extracting an organic compound from a fluid mixture of the organic compound with water, wherein the method comprises:
    contacting a nanoporous carbon membrane before its use with a pure preparation of the organic compound to be extracted to provide an activated nanoporous carbon membrane in which the pure preparation of the organic compound is adsorbed and fills pores of the membrane;
    contacting the mixture with one side of the activated nanoporous carbon membrane in which the pores of the membrane contain the adsorbed pure preparation of the organic compound;
    recovering the organic compound from the other side of the nanoporous carbon membrane, wherein the nanoporous carbon membrane is a multilayer graphene oxide (GO) or a reduced graphene oxide (rGO) membrane and the organic compound is an alcohol.

2. The method of claim 1, wherein the nanoporous carbon membrane has pore size greater than about 0.9 nm and less than about 1.5 mm.

3. The method of claim 1, wherein the alcohol is a $C_1$-$C_{12}$ alcohol.

4. The method of claim 3, wherein the $C_1$-$C_{12}$ alcohol is selected from the group consisting of methanol, ethanol, propanol, butanol, ethylene glycol, propylene glycol, glycerol, and mixtures thereof.

5. The method of claim 1, wherein the nanoporous carbon membrane is placed on a porous support layer.

6. The method of claim 1, wherein the step of contacting the mixture with one side of the activated nanoporous carbon membrane is carried out while the membrane is still wet with the pure preparation of organic compound.

7. The method of claim 1, wherein the nanoporous carbon membrane is a multilayer graphene oxide (GO).

8. The method of claim 1, wherein the nanoporous carbon membrane has a thickness from 0.05 to 1 μm.

* * * * *